United States Patent
Ryan

(10) Patent No.: US 8,202,277 B2
(45) Date of Patent: Jun. 19, 2012

(54) SMALL GAUGE SURGICAL INSTRUMENT WITH SUPPORT DEVICE

(75) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 879 days.

(21) Appl. No.: 10/844,592

(22) Filed: May 12, 2004

(65) Prior Publication Data

US 2005/0033309 A1    Feb. 10, 2005

Related U.S. Application Data

(63) Continuation-in-part of application No. 10/767,556, filed on Jan. 29, 2004, now abandoned.

(60) Provisional application No. 60/443,375, filed on Jan. 29, 2003.

(51) Int. Cl.
*A61F 9/007*    (2006.01)

(52) U.S. Cl. ......... 606/107; 606/166; 606/174; 606/205

(58) Field of Classification Search ............... 606/107, 606/130, 161, 166; 600/562–567, 570, 571
See application file for complete search history.

(56) References Cited

U.S. PATENT DOCUMENTS

| | | | | |
|---|---|---|---|---|
| 3,594,092 A | * | 7/1971 | DiCarlo | 401/258 |
| 3,736,938 A | | 6/1973 | Evvard et al. | |
| 3,942,519 A | | 3/1976 | Shock | |
| 4,256,119 A | * | 3/1981 | Gauthier | 600/567 |
| 5,139,504 A | * | 8/1992 | Zelman | 606/127 |
| 5,172,701 A | * | 12/1992 | Leigh | 600/566 |
| 5,201,741 A | * | 4/1993 | Dulebohn | 606/113 |
| 5,217,465 A | * | 6/1993 | Steppe | 606/107 |
| 5,487,725 A | * | 1/1996 | Peyman | 604/22 |
| 5,649,936 A | * | 7/1997 | Real | 606/130 |
| 5,817,111 A | * | 10/1998 | Riza | 606/148 |

* cited by examiner

Primary Examiner — Ryan Severson
(74) Attorney, Agent, or Firm — Schwegman, Lundberg & Woessner, P.A.

(57) ABSTRACT

A small gauge surgical instrument assembly is shown with advantages such as diminished "play" at the tip. A surgical instrument assembly is also shown with support along a length of the instrument that can be selected by the surgeon. In particular, very small and flexible instruments for vitreous surgery are shown with selectable stiffness, thus providing control as well as access to all parts of the vitreous cavity. Embodiments as shown are safer, and increase the variety of cases for which these instruments can be used.

8 Claims, 3 Drawing Sheets

SMALL GAUGE SURGICAL INSTRUMENT WITH SUPPORT DEVICE

RELATED APPLICATION

This application is a continuation-in-part and claims priority of invention under 35 U.S.C. §120 from U.S. application Ser. No. 10/767,556, filed Jan. 29, 2004, now abandoned which claims the benefit of U.S. Provisional Application Ser. No. 60/443,375, filed on Jan. 29, 2003, under 35 U.S.C. 119(e), the specifications of which are incorporated herein by reference.

TECHNICAL FIELD

This invention relates to small gauge instruments typically used for surgical procedures such as surgery of the eye. Specifically, this invention relates to small gauge surgical instruments for use in vitreous surgery.

BACKGROUND

Vitreous surgery was first performed in 1971, and involves the removal of the vitreous gel from the posterior aspect of the eye for treatment of a variety of disease states, including vitreous hemorrhage, macular disorders, retinal detachment, and many others. One common procedure involves the use of 3 incisions peripheral to the cornea to access the vitreous cavity. One port is used for infusion, one for illumination, and the third for suction/cutting instruments, as well as picks, scissors, forceps and others.

As the surgical approaches have evolved, smaller incisions are being used. The most common incision size currently is 20 gauge (1.0 mm diameter), but newer instruments as small as 25 gauge (0.49 mm diameter) are being introduced, and smaller instruments are likely in the future. The advantages of smaller incisions are multiple, including lessened trauma, faster healing, faster wound management (no sutures), and greater patient comfort.

Problems exist with the smaller instruments, however. The small diameter of the instruments makes them quite flexible, which is a disadvantage for the surgeon. With larger diameter instruments, there is very little "play", so the tips of the instruments go exactly where the surgeon desires that they go. With the smaller diameter instruments, the tips can move from their intended positions due to the bending or flexing of the fine wire-like instruments, which makes the surgeon feel a loss of control.

Bending or flexing of the small instruments is of particular concern during removal of peripheral vitreous, when the eye must be turned to allow viewing by the surgeon. Turning of the eye is accomplished by moving the instrument relative to the patient's head while a portion of the instrument remains inserted within a portion of the eye. Because the amount of flexing of the instrument is relatively large and unpredictable to the surgeon, precise repositioning of the eye becomes more difficult.

What is needed is an instrument design that accommodates increasingly small diameters, and still provides precise control without unwanted flexing.

DETAILED DESCRIPTION

Figure 1:
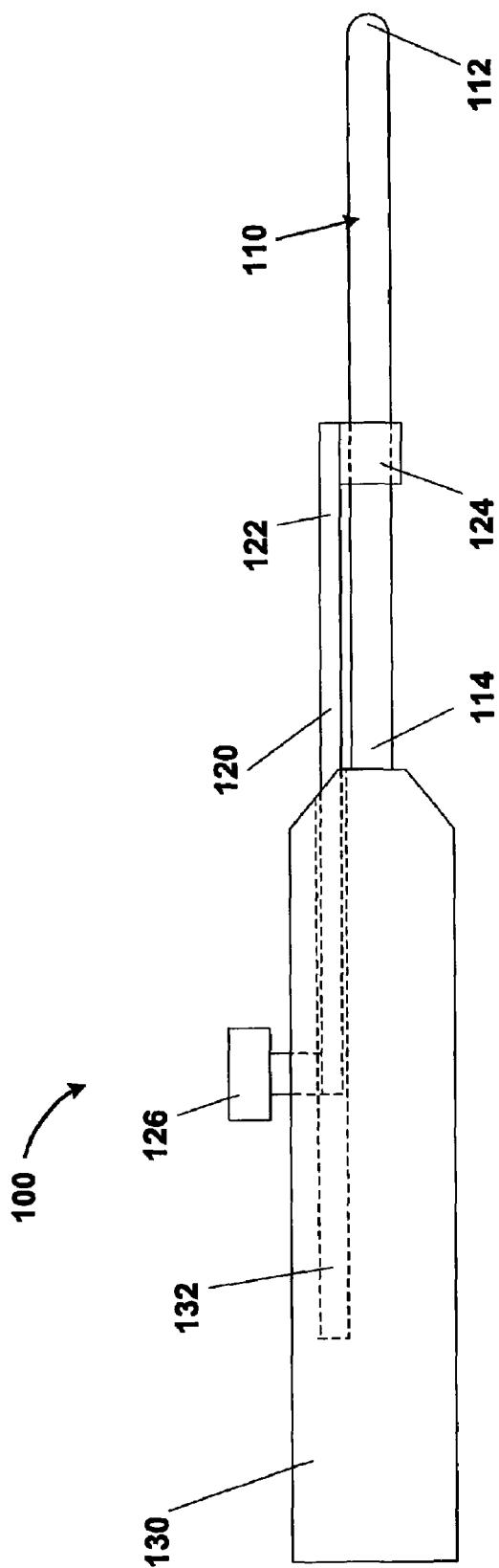
FIG. 1 shows a surgical instrument according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an instrument 100 including a small diameter instrument portion 110, and a support device portion 120. The small diameter instrument portion 110 includes a distal end 112 and a proximal end 114. In one embodiment, the small diameter instrument portion 110 includes a hollow tube. Other embodiments include, but are not limited to small diameter instrument portions such as fiber optic probes, laser guides, suction/cutting tools, forceps, scissors, etc. The small diameter instrument portion 110 shown in the Figures is drawn without specific detail of the selected instrument, however, one of ordinary skill in the art, having the benefit of the present disclosure will recognize that several small diameter instruments are possible. The small diameter instrument portion 110 and the support device portion 120 are adjustable relative to each other, allowing the surgeon to selectively provide support at different locations along a length of the small diameter instrument portion 110.

In one embodiment, a support device portion 120 of adequate stiffness is positioned along the shaft of the small diameter instrument portion 110 (25 gauge or the like). The support device portion 120 stabilizes the instrument so the surgeon using it has a greater sense of security regarding the position of the tip inside the eye. The support device portion 120 is adjustable so that the full length of the small diameter instrument portion 110 can be selectively inserted into the eye for posterior work. Posterior work typically requires minimal twisting motion by the surgeon, therefore a lower need for stabilization. Although a 25 gauge device is used as an example, the invention is not so limited. One of ordinary skill in the art, having the benefit of the present disclosure will recognize that any instrument of a smaller or larger diameter than a 25 gauge instrument will benefit from increased support depending on the forces and tolerances within a given procedure.

For peripheral vitrectomy the support device portion 120 could be moved down the shaft of the small diameter instrument portion 110 to provide increased support. With the support device portion 120 moved closer to the distal end 112, less play would be present at the distal end 112 of the small diameter instrument portion 110 when the eye is twisted and turned by the surgeon.

In one embodiment, the support device portion 120 design includes a 20 gauge cylinder 124 of a strong material such as stainless steel, to go around the small diameter instrument portion 110 (25 gauge or so). The cylinder 124 is attached to a strong shaft 122 that runs parallel to the small diameter instrument portion 110, and sits in a track 132 embedded in a handpiece 130. Although a single shaft 122 is shown, multiple shaft 122 embodiments are also within the scope of the invention. The handpiece 130 is directly attached to the small diameter instrument portion 110. The shaft 122 is of such a length that an amount of travel along the small diameter instrument portion 110 is available (for example, 10-15 mm). The amount of travel is selectable by the surgeon. A knob or other control device 126 is attached to the shaft 122, and the position of the cylinder 124 (i.e. how far down the shaft of the fine instrument it rests) is controlled by the surgeon.

In one embodiment, a number of stops lock the strut 122 in position at preset lengths, giving the surgeon varying levels of control over the flex of the small diameter instrument portion 110, while concurrently allowing the small diameter instrument portion 110 to enter the eye to various lengths, depending on the strut position. In one embodiment a clutch or set screw locks the strut 122 in position relative to the small diameter instrument portion 110.

Figure 2:
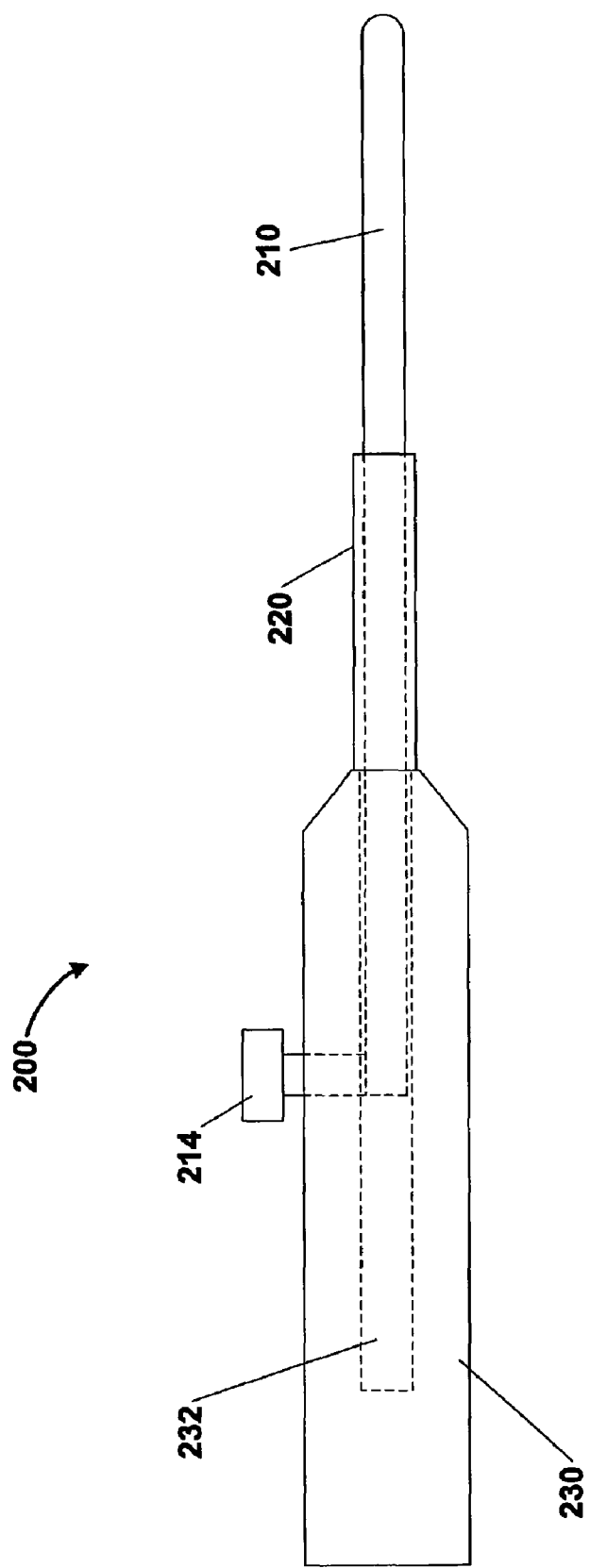
FIG. 2 shows a variation of a surgical instrument according to an embodiment of the invention.

FIG. 2 shows another embodiment of an instrument 200. In FIG. 2, a fine instrument portion 210 is the adjustable portion relative to the handpiece 230, and the support device portion 220 is fixed relative to the handpiece 230. In one embodiment, the fine instrument portion 210 is made to move within a 20 gauge or similar cylinder. Similar to embodiments described above, the fine instrument portion 210, in selected embodiments is controlled with a knob, or other control 214 within a channel 232, moved as desired by the surgeon.

Figure 3:
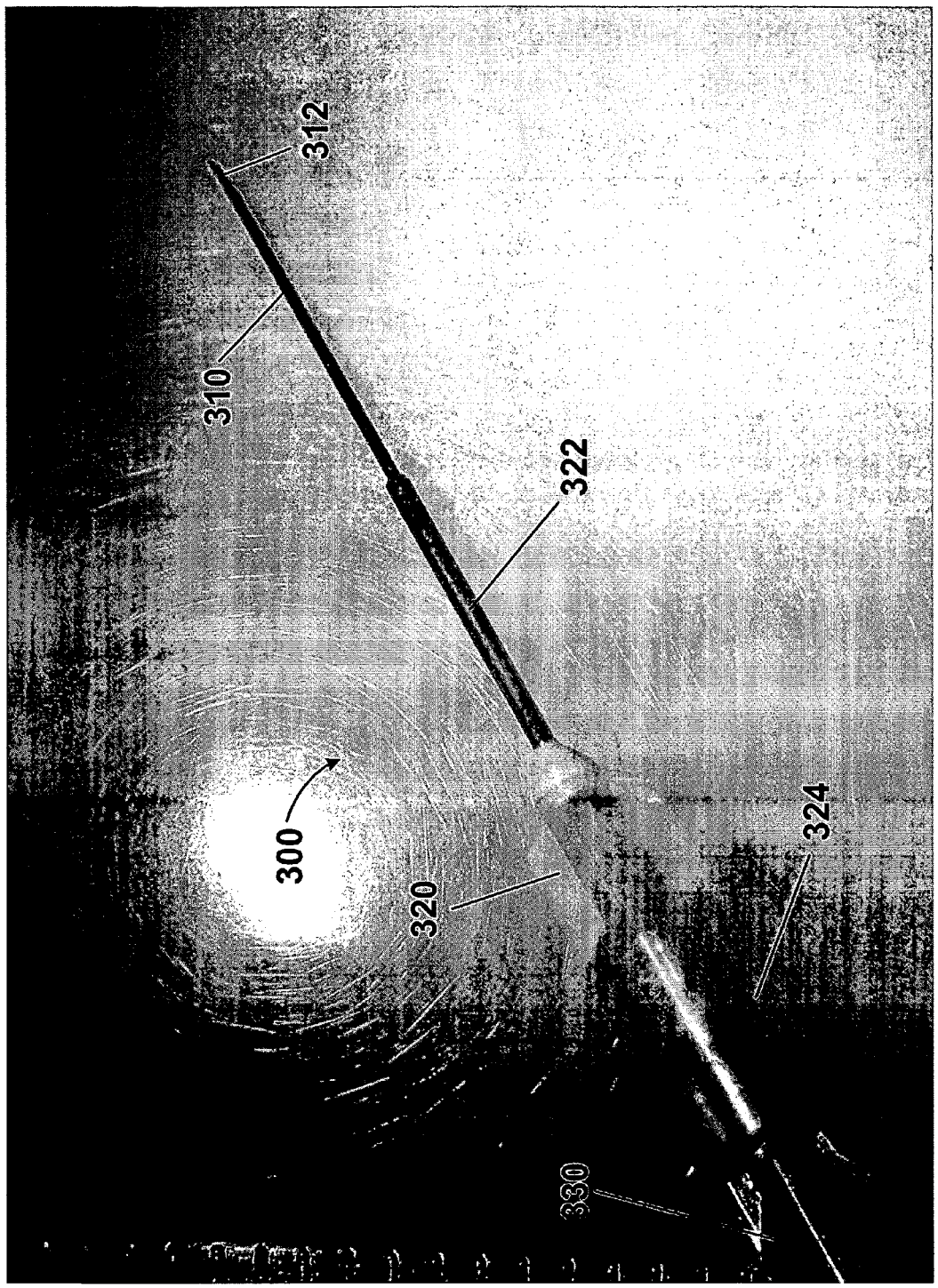
FIG. 3 shows another variation of a surgical instrument according to an embodiment of the invention.

FIG. 3 shows an instrument assembly 300. In one embodiment, a fine instrument portion 310 is coupled to a fine instrument base unit 330. In one embodiment, the base unit 330 includes a handpiece as described in embodiments above. In one embodiment, the base unit 330 and fine instrument portion 310 include existing configurations of surgical instruments such as cannulas, probes, fiber optic devices, laser guides, suction/cutting tools, forceps, scissors, etc. A distal end 312 of the fine instrument portion 310 is shown in FIG. 3 as a cutting tool or hypodermic tip example although the invention is not so limited. A support device 320 is shown in FIG. 3 as a component of the instrument assembly 300. In one embodiment, the support device 320 includes a base 324 and an extending portion 322.

In one embodiment, the extending portion 322 includes a tube with an inner diameter that closely matches an outer diameter of the fine instrument portion 310. Although a continuous tube is shown as the extending portion 322 in FIG. 3, the invention is not so limited. For example, in an alternate embodiment, a portion of a tube, or other connecting structure is coupled to a location along the length of the fine instrument portion 310. In alternate embodiments, the tube portion or other connecting structure is then coupled to the base portion 324 through an intermediate support system.

In one embodiment, the instrument assembly 300 includes multiple support devices 320 with extending portions 322 of varying lengths. In one embodiment, the instrument assembly 300 includes multiple support devices 320 with extending portions 322 of varying stiffness. In operation, one of the support devices 320 with a desired length is selected to provide the desired amount of support to the fine instrument portion 310. Other support devices 320 with different lengths are later interchanged to provide varying amounts of support and/or locations of support in one method of operation. One advantage of the instrument assembly 300 includes the ability to provide support to existing fine instrument portion configurations.

CONCLUSION

Thus has been shown, a support device which diminishes the "play" in very small and flexible instruments, such as instruments for vitreous surgery. In selected examples, a support sleeve is provided that is located around an end of a vitrectomy instrument portion adjacent to a base unit, and extending from the base unit to a location along the length of the vitrectomy instrument portion, wherein a distal end of the vitrectomy instrument portion is configured to enter an eye, while the support sleeve is configured to remain outside a surface of an eye when in use. Embodiment described above include designs where characteristics such as stiffness can be adjusted by the surgeon. Embodiments described above also include adjustments so access is possible to all parts of the vitreous cavity. Embodiments as shown above provide features to make surgical procedures safer. Embodiments described above also increase the variety of cases for which small, more flexible instruments can be used. Although vitreous surgery is discussed above as an example procedure, embodiments of the invention described above and in the following claims are not so limited. Other surgical procedures will also benefit from the advantages that these device configurations provide.

While a number of advantages of embodiments described herein are listed above, the list is not exhaustive. Other advantages of embodiments described above will be apparent to one of ordinary skill in the art, having read the present disclosure. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. A vitrectomy instrument, comprising:
   a handheld substantially rigid small diameter vitrectomy instrument portion extending from a base unit, the small diameter vitrectomy instrument portion chosen from a group consisting of fiber optic devices, laser guides, suction tools, forceps, and scissors having a length and a diameter smaller than 20 gauge;
   a support sleeve located around an end of the vitrectomy instrument portion adjacent to the base unit, and extending from the base unit to a location along the length of the vitrectomy instrument portion, wherein a distal end of the vitrectomy instrument portion is configured to enter an eye, while the support sleeve is configured to remain outside a surface of an eye when in use, wherein the support sleeve includes a tube with a constant inner diameter that contacts an outer diameter of the vitrectomy instrument portion;
   wherein a level of rigidity of the small diameter vitrectomy instrument portion is enhanced by the support sleeve.

2. The vitrectomy instrument assembly of claim 1, wherein the small diameter vitrectomy instrument portion includes a 25 gauge instrument.

3. The vitrectomy instrument assembly of claim 1, wherein the support sleeve includes a stainless steel tube.

4. The vitrectomy instrument assembly of claim 1, wherein the support sleeve includes a 20 gauge tube.

5. A vitrectomy instrument, comprising:
   a handheld substantially rigid small diameter vitrectomy instrument portion extending from a base unit, the small diameter vitrectomy instrument portion chosen from a group consisting of fiber optic devices, laser guides, suction tools, forceps, and scissors having a length and a diameter smaller than 20 gauge;

a support sleeve located around an end of the vitrectomy instrument portion adjacent to the base unit, and extending from the base unit to a location along the length of the vitrectomy instrument portion, wherein a distal end of the vitrectomy instrument portion is configured to enter an eye, while the support sleeve is configured to remain outside a surface of an eye when in use, wherein the support sleeve includes a tube wherein an inner diameter of the entire support sleeve matches an outer diameter of the vitrectomy instrument portion;

wherein a level of rigidity of the small diameter vitrectomy instrument portion is enhanced by the support sleeve.

6. The vitrectomy instrument assembly of claim 5, wherein the small diameter vitrectomy instrument portion includes a 25 gauge instrument.

7. The vitrectomy instrument assembly of claim 5, wherein the support sleeve includes a stainless steel tube.

8. The vitrectomy instrument assembly of claim 5, wherein the support sleeve includes a 20 gauge tube.

* * * * *